(12) United States Patent
Arango

(10) Patent No.: US 10,194,942 B2
(45) Date of Patent: *Feb. 5, 2019

(54) CALLUS REMOVAL APPARATUS

(71) Applicant: Alejandro Arango, Deland, FL (US)

(72) Inventor: Alejandro Arango, Deland, FL (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/655,384

(22) Filed: Jul. 20, 2017

(65) Prior Publication Data

US 2017/0312167 A1 Nov. 2, 2017

Related U.S. Application Data

(63) Continuation-in-part of application No. 15/099,013, filed on Apr. 14, 2016.

(51) Int. Cl.
*A45D 29/04* (2006.01)
*A61B 17/54* (2006.01)
(Continued)

(52) U.S. Cl.
CPC .............. *A61B 17/54* (2013.01); *A45D 29/04* (2013.01); *A47K 7/026* (2013.01); *A61B 2017/00747* (2013.01); *A61B 2017/320004* (2013.01); *A61B 2017/320008* (2013.01); *A61H 2201/1692* (2013.01); *A61K 2800/28* (2013.01)

(58) Field of Classification Search
CPC ................. A45D 29/04; A61B 17/54; A61B 2017/00752; A61B 2017/00747; A61B 2017/00761; A61B 2017/32008; B26B 19/14–19/148; B27G 17/04; B44D 3/162; B44D 3/164

USPC ..... 132/75.3, 75.4, 75.5, 75.6, 76.4; D28/59; D24/146, 147, 149; D7/678; 241/273.1, 241/273.2, 273.3, 273.4
See application file for complete search history.

(56) References Cited

U.S. PATENT DOCUMENTS

D49,710 S * 9/1916 Lupo ............................. D28/59
1,620,825 A * 3/1927 Mills ....................... B29C 73/26
81/15.2

(Continued)

OTHER PUBLICATIONS

AMOS Foot Rasp Callus File Dry Hard Dead Skin Corn Remover, https://www.amazon.co.u/AMOS-Callous-Exfoliating-Pedicure-SMoother/dp/B00EDJSB14, p. 1-6, Aug. 17, 2015 (see comments on p. 6).*

*Primary Examiner* — Tatiana Nobrega

(74) *Attorney, Agent, or Firm* — Glenn E. Gold, P.A.; Glenn E. Gold

(57) ABSTRACT

A callus removal apparatus includes a main body having opposite first and second end portions and an elongated configuration for ease of gripping by one hand, a callus scraping device fitted on the main body first end portion, and a callus sanding device fitted on and detachable from the main body second end portion. The callus scraping device has a head with an array of spaced-apart punched-through projections that extend upwardly from the head and have a plurality of jagged edges at a distal end thereof. The exposed projections are capable of removing pieces of a callus by moving the head across and in contact with the callus. The callus sanding device has a panel and a plurality of sanding particles attached on the panel and exposed at the exterior thereof and thus capable of removing pieces of a callus moving the panel across and in contact with the callus.

14 Claims, 15 Drawing Sheets

(51) Int. Cl.
*A47K 7/02* (2006.01)
*A61B 17/00* (2006.01)
*A61B 17/32* (2006.01)

(56) References Cited

U.S. PATENT DOCUMENTS

| | | | | |
|---|---|---|---|---|
| 2,231,453 A | * | 2/1941 | Pitar | A45D 26/0004 |
| | | | | 451/524 |
| D186,752 S | * | 11/1959 | Dean | 30/26 |
| 4,037,793 A | * | 7/1977 | Puustinen | A47J 43/25 |
| | | | | 241/168 |
| 4,211,246 A | * | 7/1980 | Hokama | A45D 29/12 |
| | | | | 132/76.4 |
| D276,276 S | * | 11/1984 | Bankier | D24/147 |
| 4,807,360 A | * | 2/1989 | Cerier | B26B 21/20 |
| | | | | 30/346.5 |
| D412,764 S | * | 8/1999 | Godbout | D28/59 |
| 6,470,895 B1 | * | 10/2002 | Miller | A61B 17/54 |
| | | | | 132/75.6 |
| D596,353 S | * | 7/2009 | Yang | D24/147 |
| D596,802 S | * | 7/2009 | Yang | D24/147 |
| D605,001 S | * | 12/2009 | Eide | D7/678 |
| D623,801 S | * | 9/2010 | Curran | D24/147 |
| D631,199 S | * | 1/2011 | Helm | D28/59 |
| D643,153 S | * | 8/2011 | Howlett | D24/147 |
| D739,981 S | * | 9/2015 | Lee | D28/59 |
| D740,490 S | * | 10/2015 | Roberts | D28/59 |
| D741,017 S | * | 10/2015 | Exley | D28/59 |
| 2008/0091216 A1 | * | 4/2008 | Grace | A61B 17/54 |
| | | | | 606/131 |
| 2009/0198159 A1 | * | 8/2009 | Linzell | A61H 7/003 |
| | | | | 601/138 |
| 2010/0037906 A1 | * | 2/2010 | Ionis | A61B 17/54 |
| | | | | 132/76.5 |
| 2010/0217357 A1 | * | 8/2010 | Da Silva | A61B 17/54 |
| | | | | 607/88 |
| 2012/0179170 A1 | * | 7/2012 | Payne | A45D 26/00 |
| | | | | 606/133 |
| 2018/0092448 A1 | * | 4/2018 | Johnson | A45D 29/04 |

* cited by examiner

CALLUS REMOVAL APPARATUS

CROSS REFERENCE TO RELATED APPLICATION(S)

This U.S. non-provisional patent application is a continuation-in-part of, and claims priority to, co-pending U.S. non-provisional patent application Ser. No. 15/099,013, having a filing date of Apr. 14, 2016, the entire contents of which are incorporated-by-reference herein.

FIELD OF THE INVENTION

The present invention relates to calluses on hands and feet, and, more particularly, is concerned with an apparatus for removal of calluses, such as from hands and feet.

BACKGROUND OF THE INVENTION

Hyperkeratosis is a thickening and hardening of the outer layer of a person's skin. The outer layer of skin contains a tough, protective protein called keratin. Skin thickening and hardening is a normal response against application of abnormal pressure and friction from rubbing on an area of skin, such as the result of the person's hands and feet being used in the performance of hard work and labor. The abnormal pressure and friction causes the skin to form a hard, protective surface, a callus.

Repeated handling of an object that puts abnormal pressure and/or creates abnormal friction on the hands, such as from tools, sports equipment and the like, typically causes calluses on the hands. Abnormal pressure and friction created by footwear or by walking barefoot causes calluses on the feet.

One conventional process of removing a callus has the following three steps. First, soaking the callused feet/hands with a solution containing baking soda or Epsom salts for half an hour or so to soften the hardened skin. Second, scrubbing the callused feet/hands using a file or pumice stone to remove the calluses. Third, drying the feet/hands and then sprinkling them with a small amount of cornstarch. However, many persons don't have time to follow this lengthy process and so seek to find an alternative approach that can be used equally well to remove calluses in much less time.

Accordingly, there remains a need in the art for an innovation that will overcome the deficiencies of past approaches and the problems that remain unsolved.

SUMMARY OF THE INVENTION

The present invention is directed to an innovation that overcomes the deficiencies of the known art and the problems that remain unsolved by providing an apparatus for removal of calluses, such as from hands and feet. The apparatus is small in size, and can work in all directions and in hard to get at places to remove calluses.

In one aspect of the present invention, a callus removal apparatus includes:
  a main body having opposite first and second end portions and an elongated configuration for ease of gripping with one hand;
  a callus scraping device fitted on the first end portion of the main body, the callus scraping device comprising
    a head having an exterior surface and interior surface, and an array of spaced-apart punched-through projections extending upwardly from the exterior surface of the head and having a plurality of jagged edges at a distal end thereof, the head being capable of contacting, and removing pieces of, a callus by moving the head across and in contact with the callus; and
  a callus sanding device fitted on the second end portion of the main body, the callus sanding device comprising
    a panel having an exterior face, and
    a plurality of sanding particles attached on said exterior face of said panel and exposed at the exterior thereof and thus capable of contacting, and removing pieces of, a callus by moving the panel across and in contact with the callus.

In another aspect of the present invention, the main body is hollow, and the first end portions of the main body has an annular end face and an annular ledge on an inside of the first end portion being spaced longitudinally along the first end portion from said annular end face and extending inwardly from the first end portion such that an annular recess is formed on the inside of and about said first end portion and extends longitudinally from said annular end face to said annular ledge.

In another aspect of the present invention, the spaced-apart punched-through projections are provided in an annular configuration and radiate outwardly from a peak on the head to approximately an annular peripheral edge of the head, the annular peripheral edge surrounding the exterior and interior surfaces and the plurality of spaced-apart punched-through projections which extend between the interior and exterior surfaces of the head providing a plurality of corresponding spaced-apart apertures.

In another aspect of the present invention, the callus scraping device also comprises a connector fixedly attached to the interior face of the head inside of the annular peripheral edge of the head, surrounding the plurality of spaced-apart punched-through projections, and extending away from the head so as to snugly fit within the first end portion of the main body as at least one of the annular peripheral edge portions of the head makes contact with the annular end face of the main body or the connector at a rear end thereof makes contact with the annular ledge on the inside of the first end portion of the main body.

In another aspect of the present invention, the main body is hollow, and the callus sanding device is also joined with an end cap at one end fitted on the second end portion of the main body and detachable from the main body to remove callus pieces from the main body, the end cap at an opposite end supporting said panel.

In another aspect of the present invention, the main body is hollow, and the second end portion of said main body has an annular end face and an annular ledge on an outside of the second end portion being spaced longitudinally along the second end portion from the annular end face and extending outwardly from the second end portion such that an annular recess is formed outside of and about the second end portion and extends longitudinally from the annular end face to the annular ledge. The panel of the callus sanding device also has an interior face and an annular peripheral rim portion surrounding said exterior and interior faces and said plurality of sanding particles on said exterior face, wherein the annular peripheral rim portion of the panel is supported at a top surface of a second recess on the end cap; and the callus sanding device is also joined with an end cap received in the annular recess so as to snugly fit about the outside of the second end portion as the end cap makes contact with the annular ledge on the outside of the second end portion of the main body.

In another aspect of the present invention, a callus removal device includes:

A callus removal apparatus, comprising:

a hollow main body having opposite first and second end portions and an elongated configuration for ease of gripping said hollow main body with one hand;

a callus scraping device fitted on said first end portion of said main body, said callus scraping device comprising a head having a convex-shaped exterior surface and a concave-shaped interior surface, and an array of spaced-apart punched-through projections extending upwardly from the exterior surface of the head and having a plurality of jagged edges at a distal end thereof, the head being capable of contacting, and removing pieces of, a callus by moving the head across and in contact with the callus; and an end cap fitted on and enclosing said second end portion of said hollow main body and being detachable from said hollow main body to remove callus pieces from said hollow main body.

In another aspect of the present invention, a callus removal device includes:

a callus removal apparatus, comprising:

a hollow main body having opposite first and second end portions and an elongated form for ease of gripping said hollow main body with one hand;

a callus scraping element disposed on said first end portion of said main body, said callus scraping element comprising a head having a convex-shaped exterior surface and a corresponding concave-shaped interior surface, and an array of spaced-apart punched-through projections extending upwardly from the exterior surface of the head, each punched-through projection terminating at a jagged peripheral edge at a distal end thereof, the head being capable of frictionally contacting, and removing pieces of, a callus via frictional rubbing engagement of the head with an exterior surface of the callus; and an end cap fitted upon and enclosing said second end portion of said hollow main body and being detachable from said hollow main body to remove callus pieces from an interior space of said hollow main body.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Figure 1:
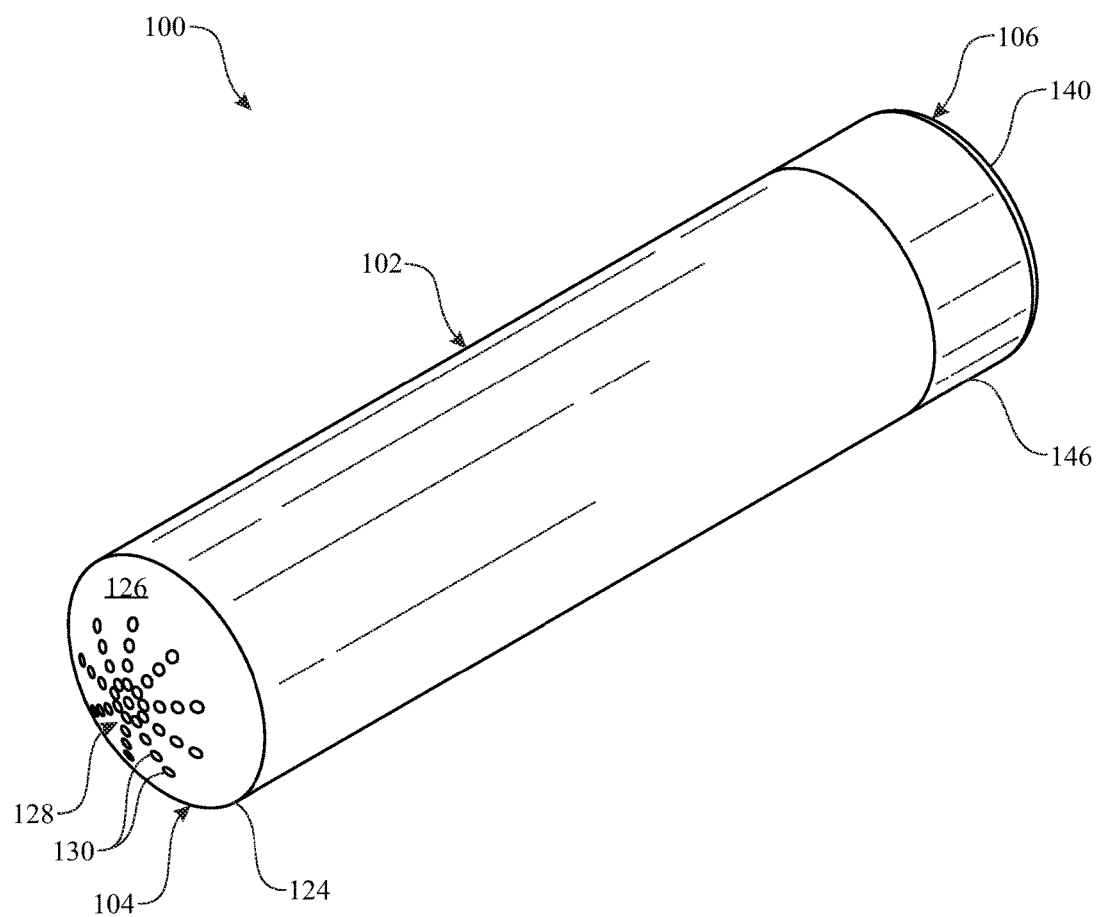
FIG. 1 presents an isometric assembled view of an exemplary embodiment of a callus removal apparatus, being shown from a callus scraping device end of the apparatus.
Figure 2:
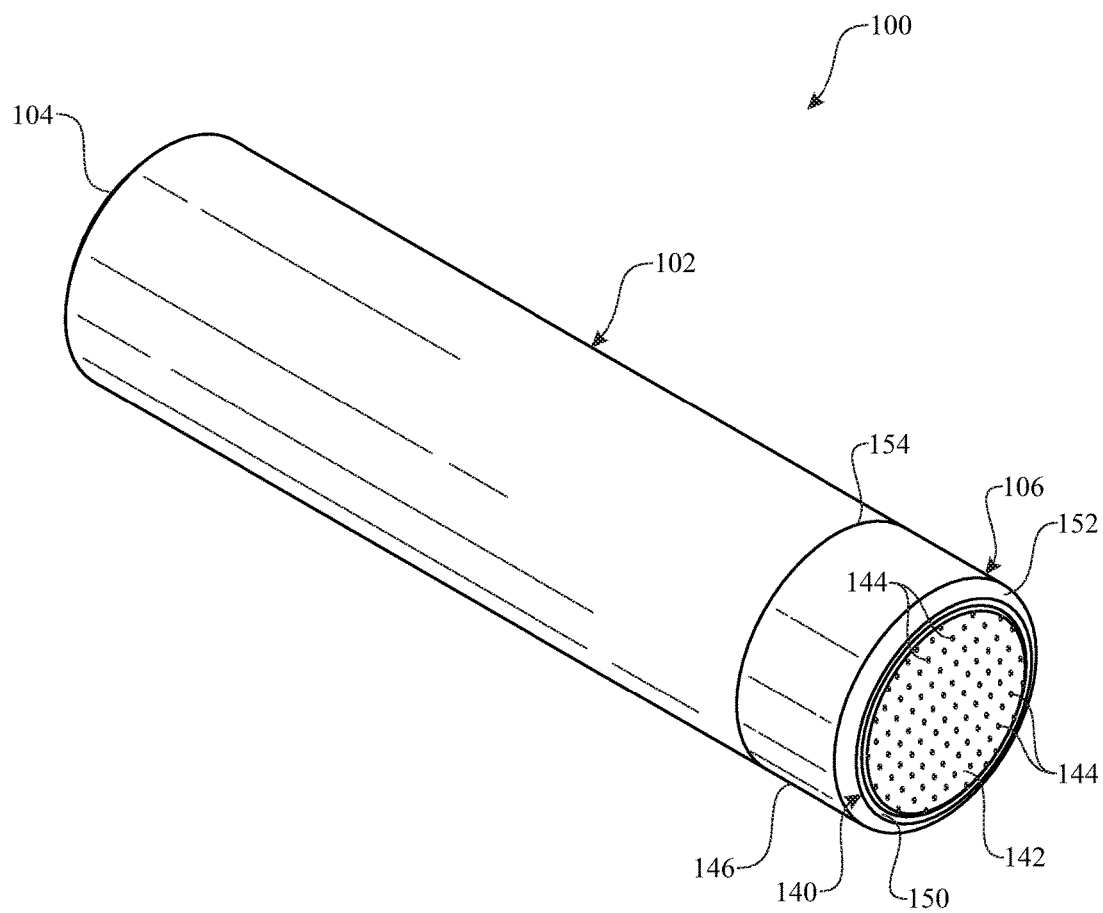
FIG. 2 presents another isometric assembled view of the callus removal apparatus, being shown from a callus sanding device end of the apparatus.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-6, there is illustrated an exemplary embodiment of a callus removal apparatus, generally designated 100, in accordance with aspects of the present invention. The illustrated callus removal apparatus 100 includes a main body 102, a callus scraping device 104, and a callus sanding device 106. The main body 102 has opposite first and second end portions 108, 110. Also, the main body 102 is hollow, made from a suitable plastic or metal, and of an elongated cylindrical shape for ease of gripping with one hand. The callus scraping device 106 is made of a suitable metal and fitted on the first end portion 108 of the main body 102. The callus sanding device 106, in part, is made of a suitable plastic or metal and fitted on the second end portion 110 of the main body 102.

Figure 3:
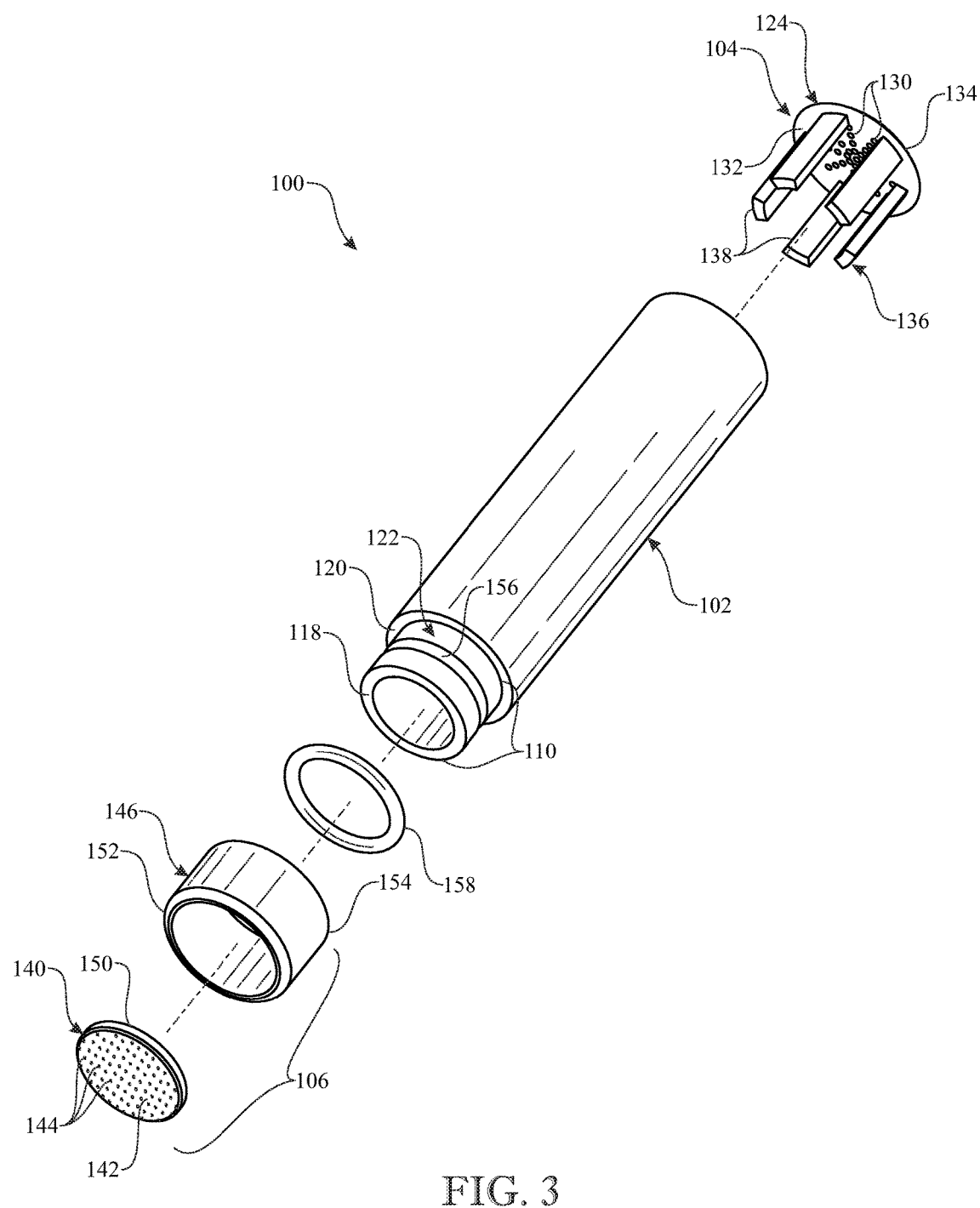
FIG. 3 presents an isometric exploded view of the callus removal apparatus, being shown as originally introduced in FIG. 1.
Figure 4:
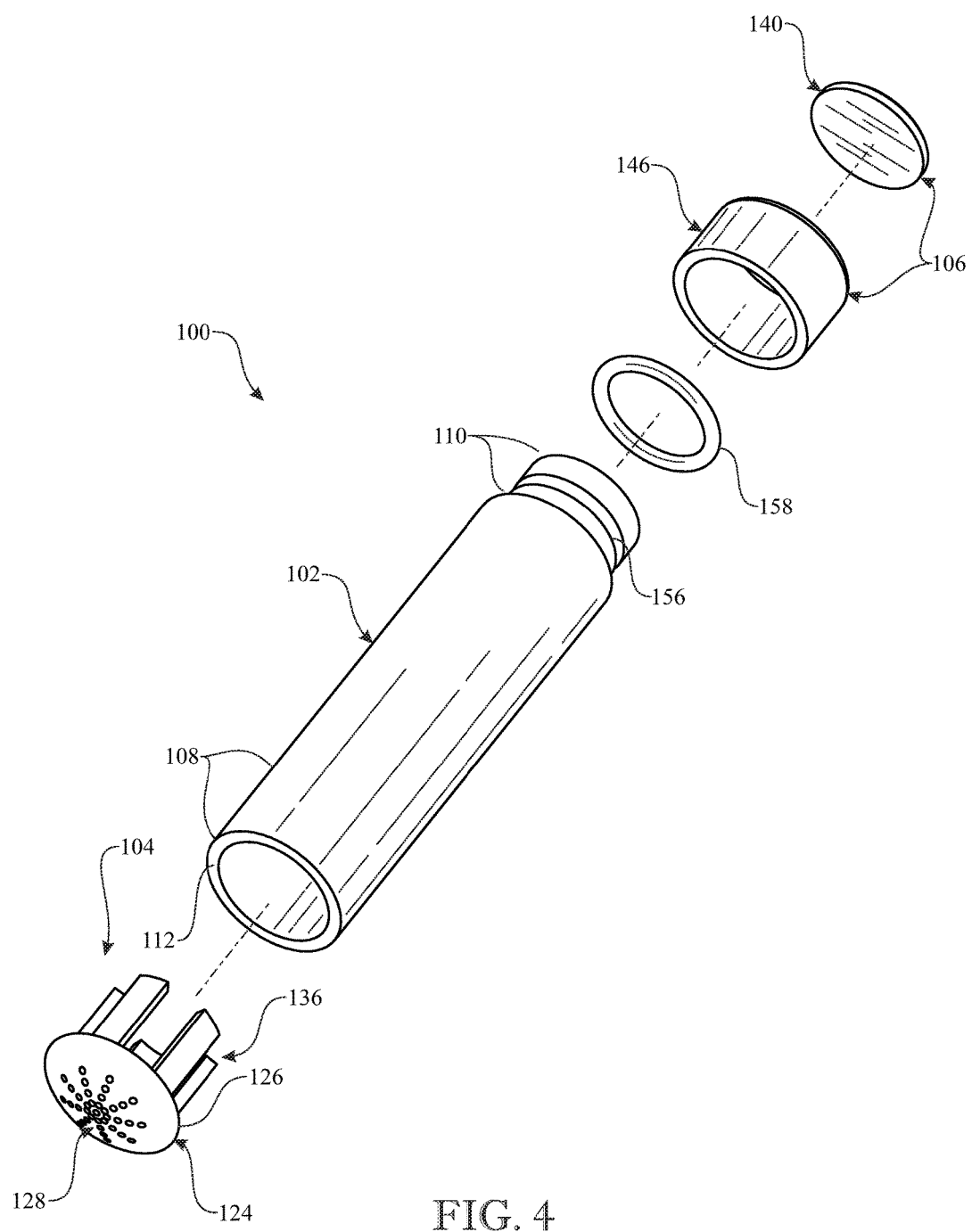
FIG. 4 presents another isometric exploded view of the callus removal apparatus, being shown as originally introduced in FIG. 2.
Figure 5:
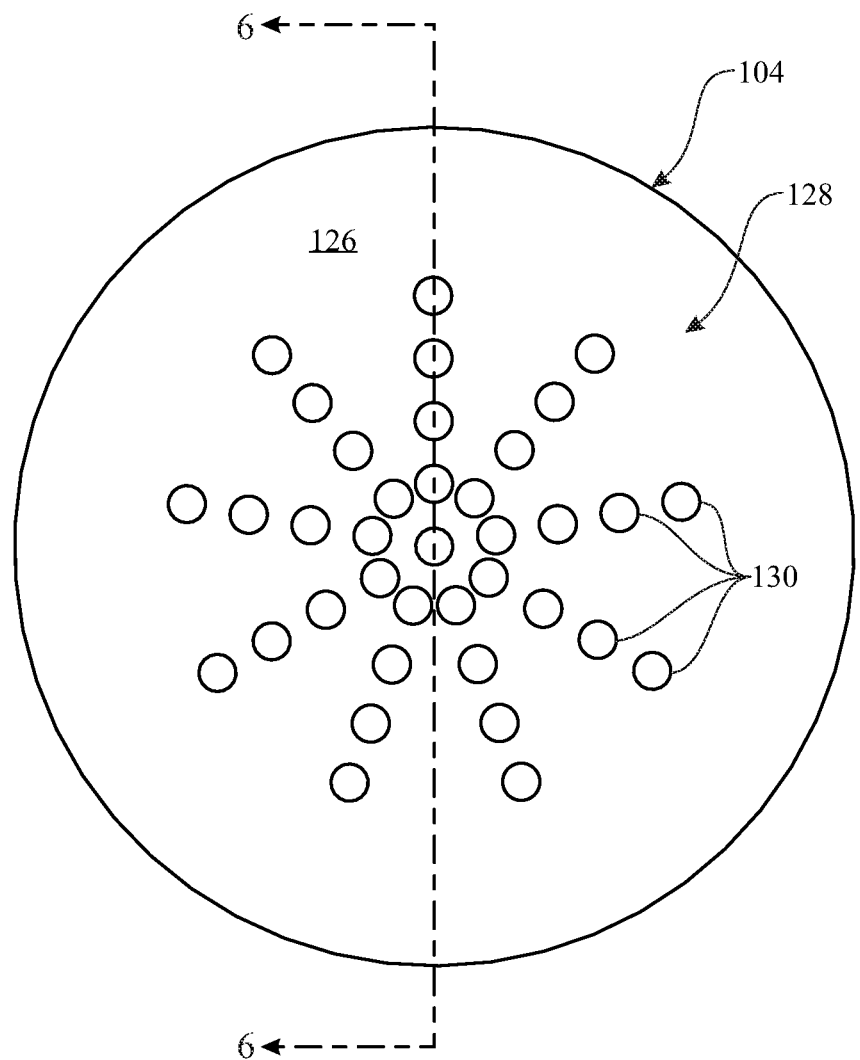
FIG. 5 presents the a front plan view of the callus removal apparatus, being shown from the callus scraping device end of the apparatus.
Figure 6:
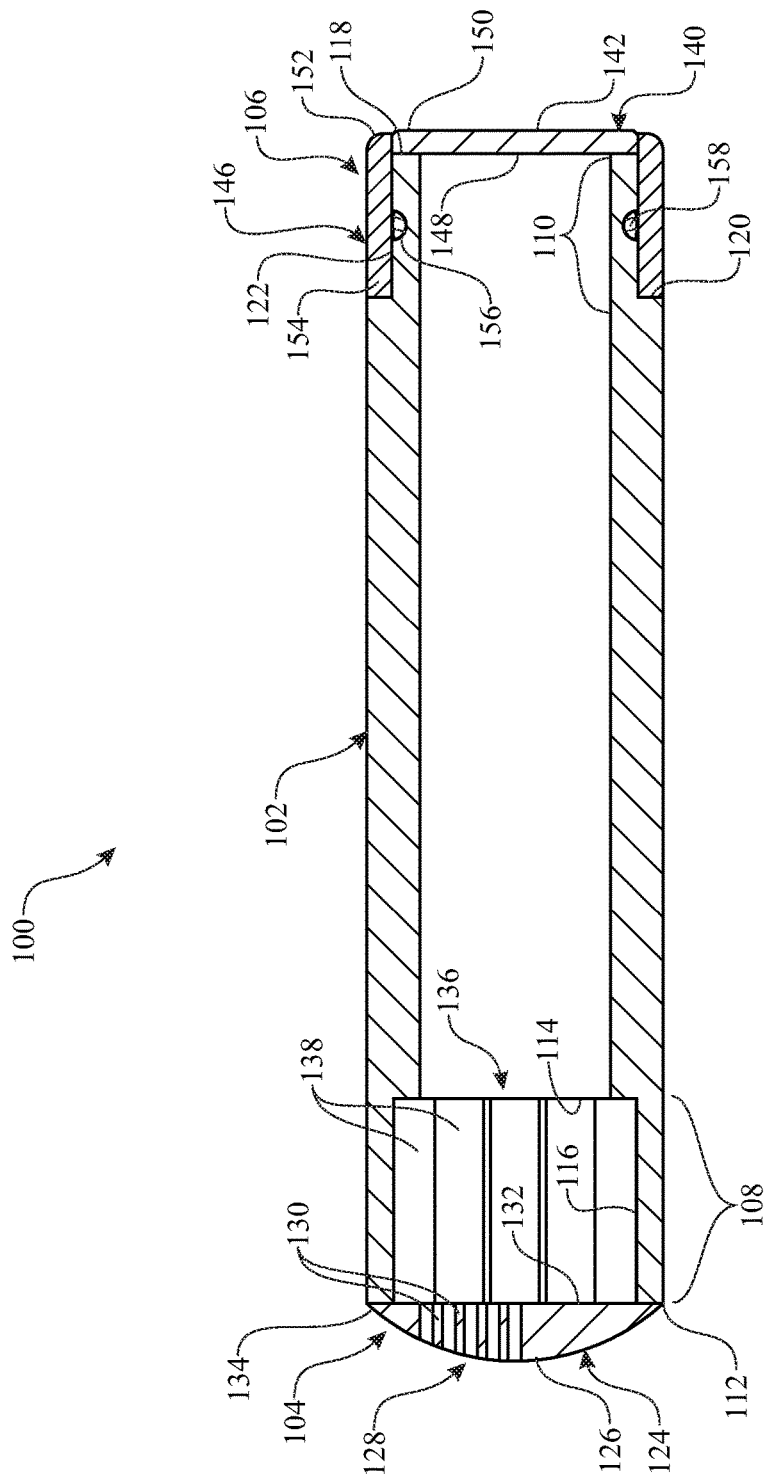
FIG. 6 presents a longitudinal sectional assembled view of the callus removal apparatus taken along section line 6-6 in FIG. 5.

More particularly, as best seen in FIGS. 4 and 6, the first end portion 108 of the main body 102 has an annular end face 112 and an annular ledge 114 on the inside of the first end portion, being spaced longitudinally along the first end portion 108 from the annular end face 112 and extending inwardly from the first end portion such that an annular recess 116 is formed on the inside of and about the first end portion 108 and extends longitudinally from the annular end face 112 to the annular ledge 114. As best seen in FIGS. 3 and 6, the second end portion 110 of the main body 102 has an annular end face 118 and an annular ledge 120 on the outside of the second end portion, being spaced longitudinally along the second end portion 110 from the annular end face 118 and extending outwardly from the second end portion such that an annular recess 122 is formed outside of and about the second end portion 110 and extends longitudinally from the annular end face 118 to the annular ledge 120.

Figure 8:
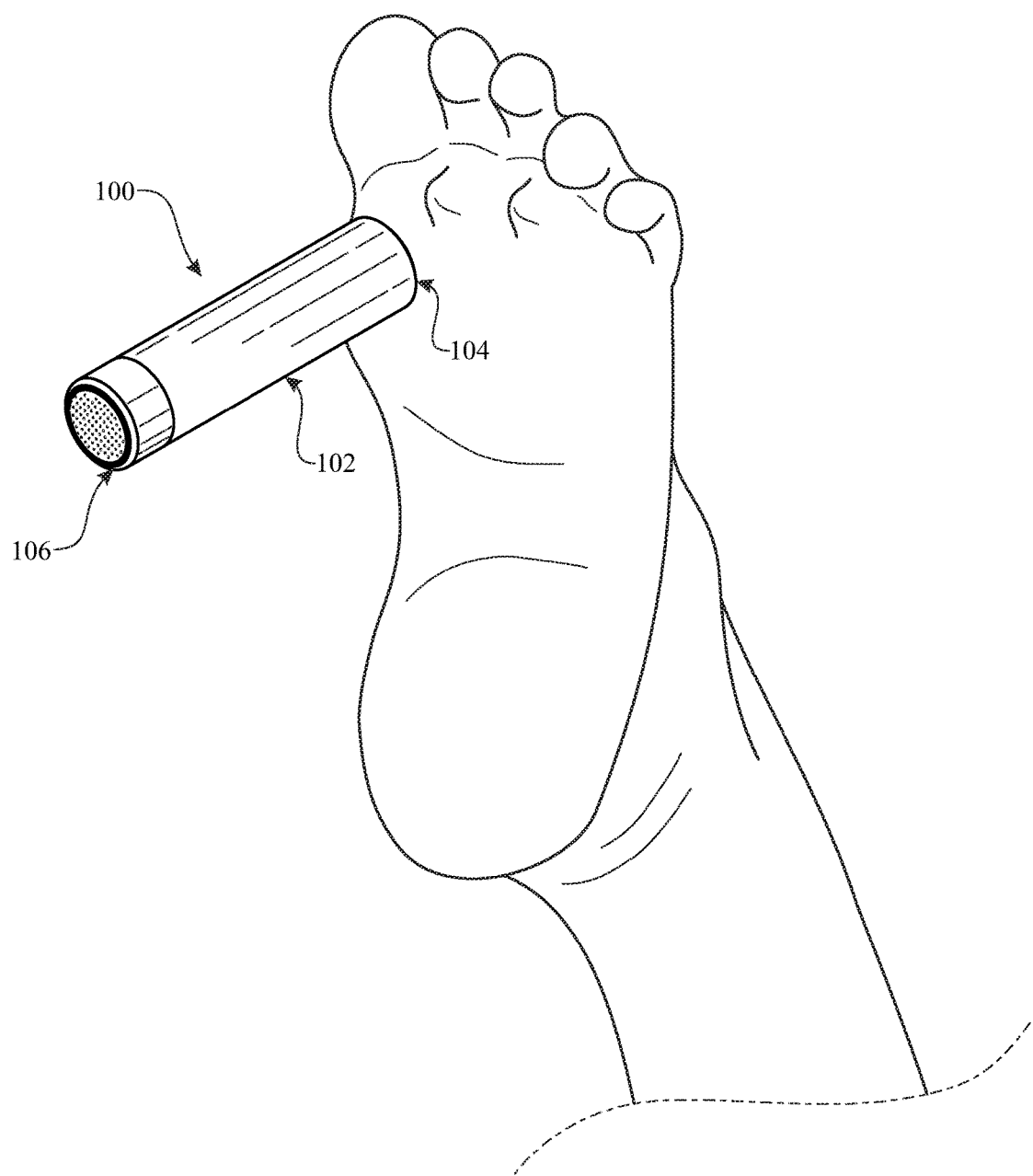
FIG. 8 presents a perspective view of the callus removal apparatus, showing the callus scraping device end of the apparatus being used to remove a callus from a person's foot.
Figure 9:
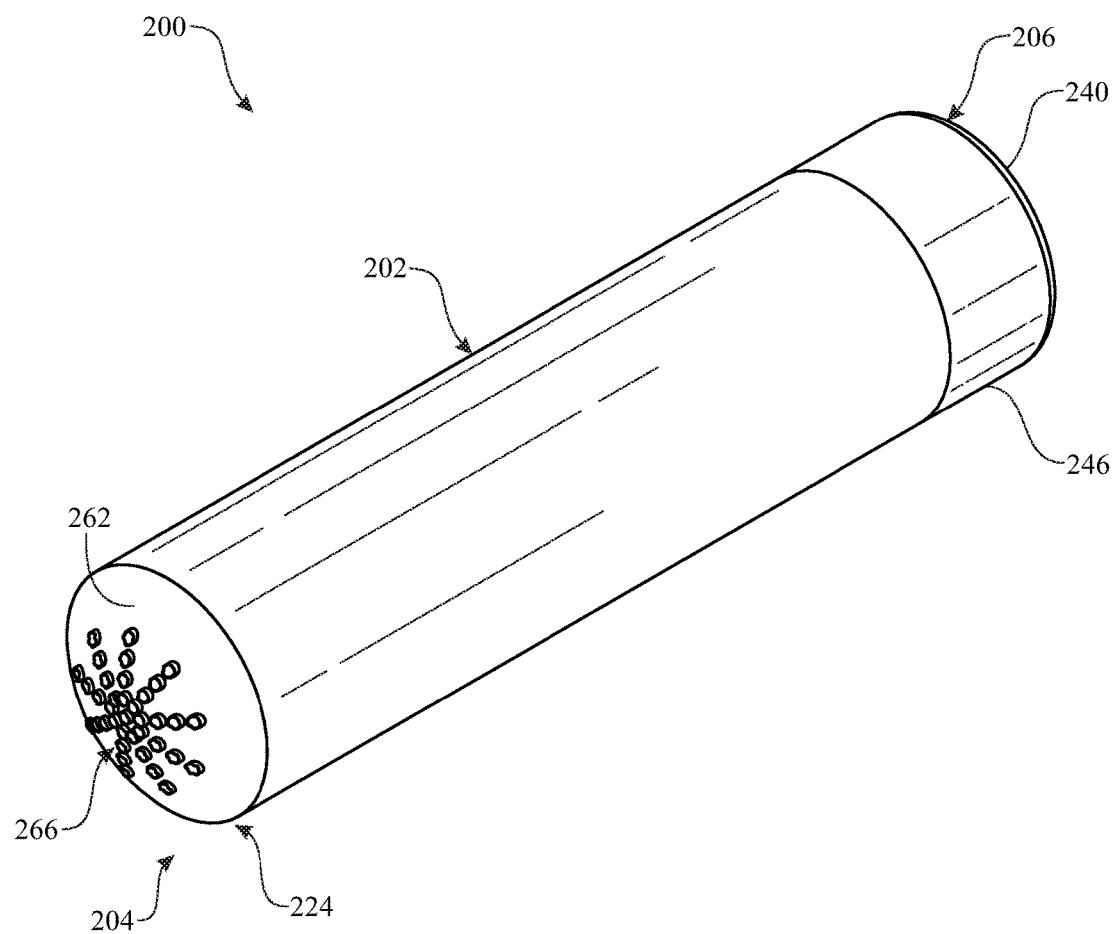
FIG. 9 presents an isometric assembled view of an alternate exemplary embodiment of a callus removal apparatus, being shown from a callus scraping device end of the apparatus.
Figure 10:
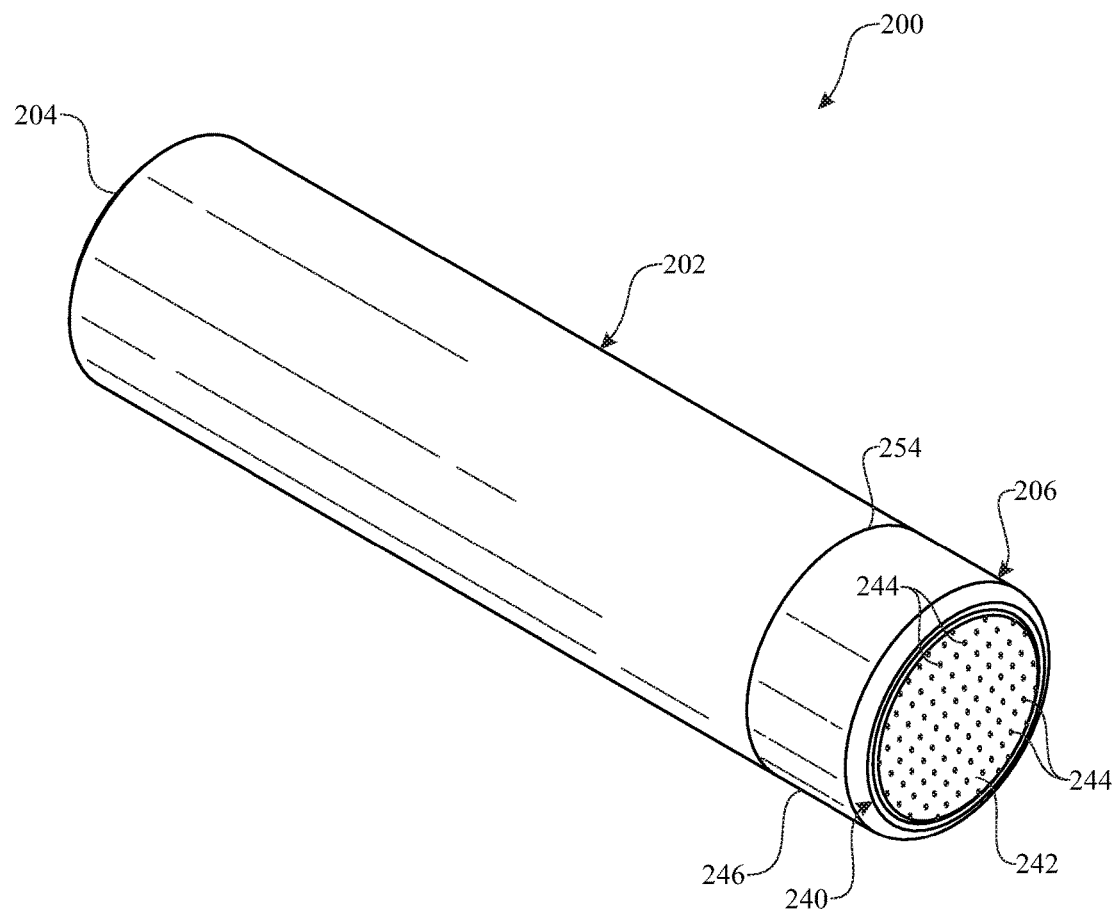
FIG. 10 presents another isometric assembled view of the alternate embodiment of the callus removal apparatus, being shown from a callus sanding device end of the apparatus.
Figure 11:
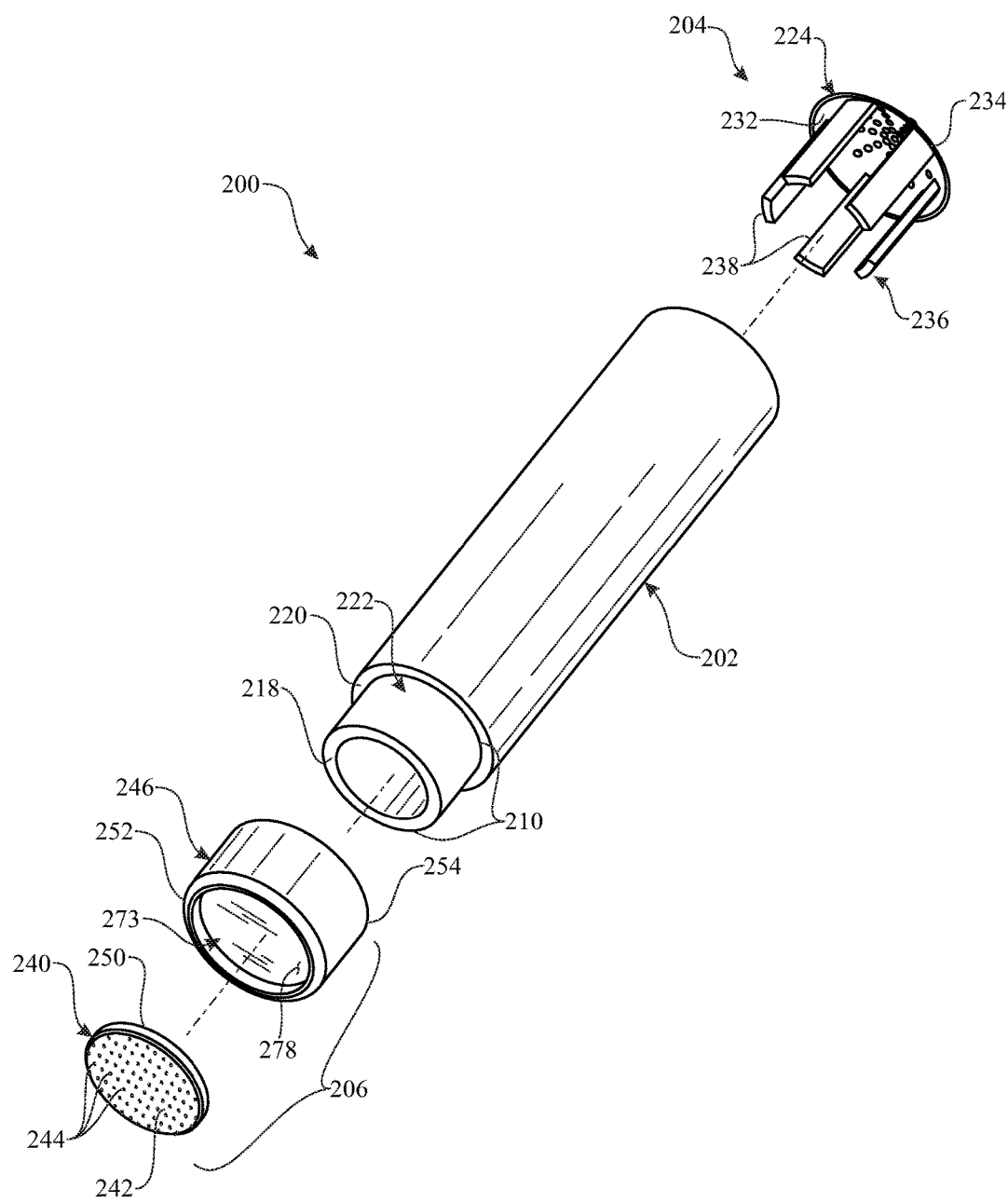
FIG. 11 presents an isometric exploded view of the alternate embodiment of the callus removal apparatus as originally introduced in FIG. 9.

The callus scraping device 104 basically includes a head 124 having an exterior face 126, and an array of spaced apart annular edges 128 exposed at the exterior face that form a plurality of spaced apart apertures 130 extending through the head 124. The exterior face 126 being of convex or dome shape and the spaced apart annular-shaped edges 128 being exposed at the exterior face of the head 124 renders the edges 128 in the exterior face 126 capable of contacting and removing pieces of a callus by gripping the main body 102 with one hand and moving and scraping its head 124, in any direction, across and in contact with a callus, such as shown in FIG. 8. In the one exemplary embodiment seen in FIGS. 1, 4 and 5, the spaced apart apertures 130 are aligned in a plurality of rows intersecting at and radiating outward from a central one of the apertures. Also, the dome-shaped head 124 with the annular edges 128 may be in the form of a cutting screen.

The head 124 of the callus scraping device 104 also has an interior face 132 and an annular peripheral rim portion 134 surrounding the exterior and interior faces 126, 132 and the plurality of spaced apart apertures 130 which extend between the exterior and interior faces of the head. The callus scraping device 104 also includes a connector 136 in the form of a plurality of legs 138 arranged spaced apart from one another in a circular row and fixedly attached to the interior face 132 of the head 124, inwardly of the annular peripheral rim portion 134 of the head and surrounding the plurality of spaced apart apertures 130, so as to extend away from the head. The legs 138 are made of a resilient springy material so that they will yield sufficiently inwardly to snugly fit within the first end portion 108 of the hollow main body 102 as at least one of the annular peripheral rim portion 134 of the head 124 makes contact with the annular end face 112 of the main body 102 or the connector 136 at a rear end thereof makes contact with the annular ledge 114 on the inside of the first end portion 108 of the main body.

Figure 7:
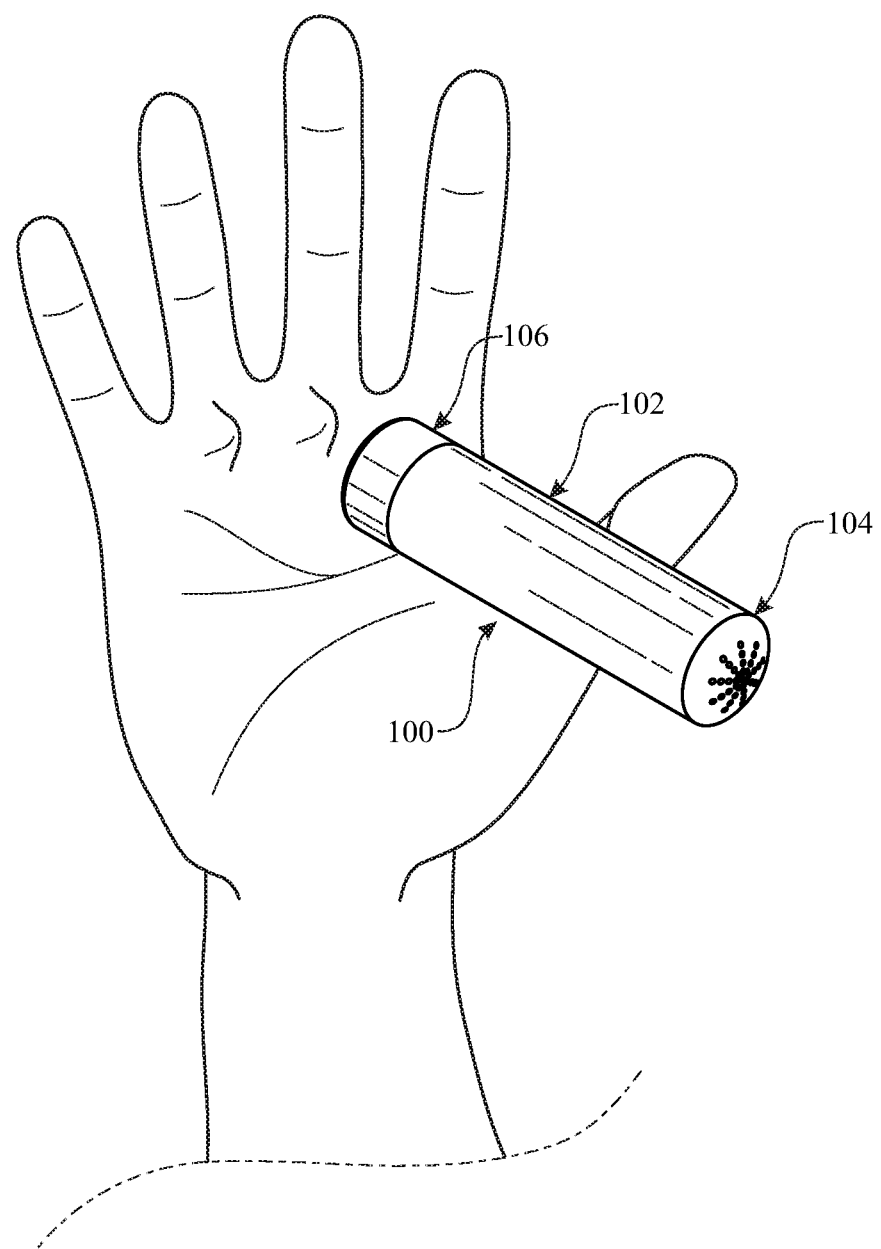
FIG. 7 presents a perspective view of the callus removal apparatus, showing the callus sanding device end of the apparatus being used to remove a callus from a person's hand.

The callus sanding device 106 basically includes a panel 140 having an exterior face 142, and a plurality of sanding particles 144 attached on the exterior face of the panel and exposed at the exterior thereof and thus capable of contacting, and removing pieces of, a callus by gripping the main body 102 with one hand and moving the panel 140 across and in contact with the callus, as shown in FIG. 7. The panel 140 with the sanding particles 144 may be in the form of a piece of 80 GHT sandpaper. Alternatively, the callus removal apparatus 100 may have a hollow end cap 146, with or without the sanding panel 140, fitted on and enclosing the second end portion 110 of the main body 102. The end cap 146 may also be detachable from the second end portion 110 of the main body 102 to remove callus pieces from the hollow main body.

The panel 140 of the callus sanding device 106 also has an interior face 148 and an annular peripheral rim portion 150 surrounding the exterior and interior faces 142, 148 and the plurality of sanding particles 144 on the exterior face. The callus sanding device 106 may also be joined with the hollow end cap 146 received in the annular recess 122 so as to snugly fit about the outside of the second end portion 110 of the main body 102 as at least one of the annular peripheral rim portion 150 of the panel 140 supported at one end 152 of the hollow end cap 146 makes contact with the annular end face 118 of the second end portion 110 of the main body 102 or an opposite end 154 of the hollow end cap 146 makes contact with the annular ledge 120 on the outside of the second end portion 110 of the main body 102. The main body 102 also has an annular groove 156 formed in the second end portion 110 and about the annular recess 122, and an O-ring 158 seated and compressed in the annular groove 156 when the hollow end cap 146 is snugly fitted along the annular recess 122 about the outside of the second end portion of the main body. The presence of the annular groove 156 and O-ring 158 enables ease of removal and replacement of the end cap 146 from and back on the second end portion 110 of the main body 102 of the callus removal apparatus 100.

Referring now to FIGS. 9 through 14, there is illustrated an alternate exemplary embodiment of a callus removal apparatus, now generally designated reference numeral 200, in accordance with the aspect of the present invention. Like features of the callus removal apparatus 100 and 200 are numbered the same except preceded by the numeral '2'. The callus removal 200 includes a main body 202, a callus scraping device 204, and a callus sanding device 206. The main body 202 has opposite first and second end portions 208 and 210. Also, the main body 202 is hollow having elongated cylindrical shaped body for ease of gripping with one hand and can be constructed generally from a suitable plastic or metal material. The callus scraping device 206 is made of a suitable metal and fitted on the first end portion 208 of the main body 102. The callus sanding device 206, in part, is generally made of a suitable plastic or metal material and is fitted on the second end portion 210 of the main body 202.

Figure 12:
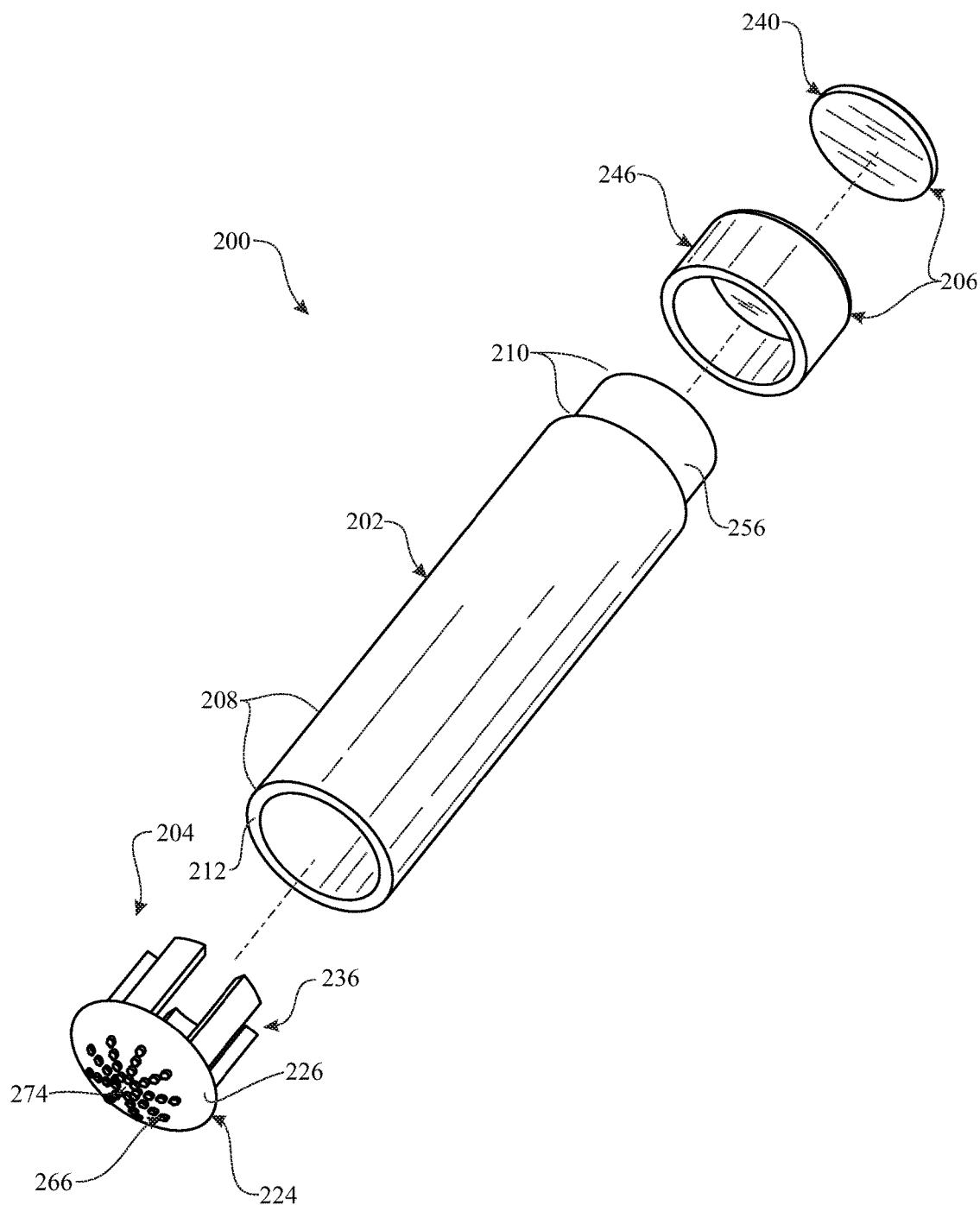
FIG. 12 presents an isometric exploded view of the alternate embodiment of the callus removal apparatus as originally introduced in FIG. 10.
Figure 13:
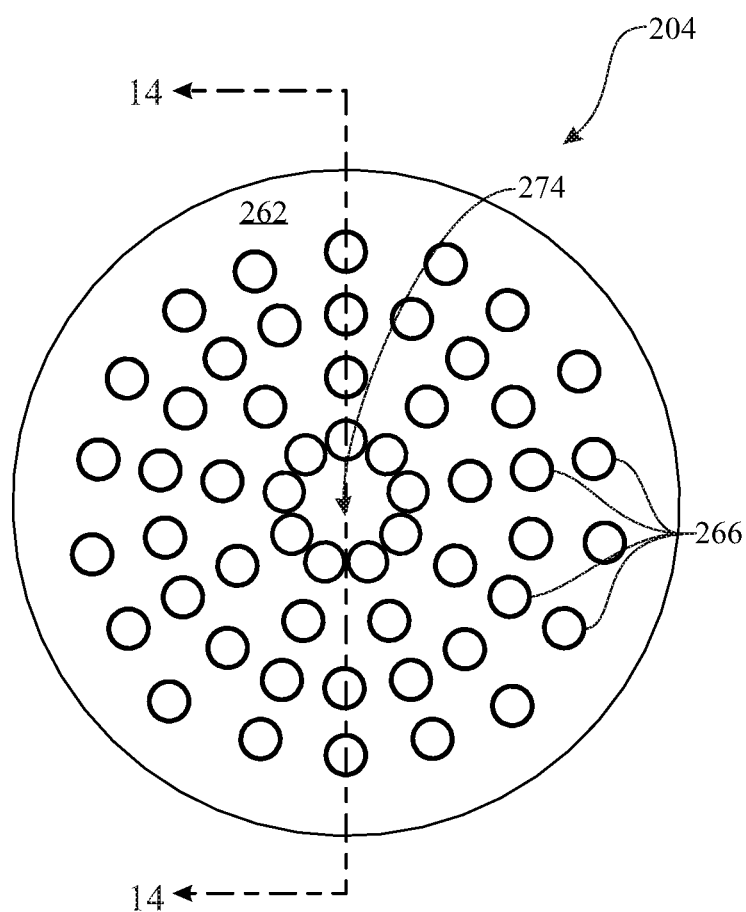
FIG. 13 presents a front plan view of the callus removal apparatus, being shown from the callus scraping device end of the apparatus.
Figure 14:
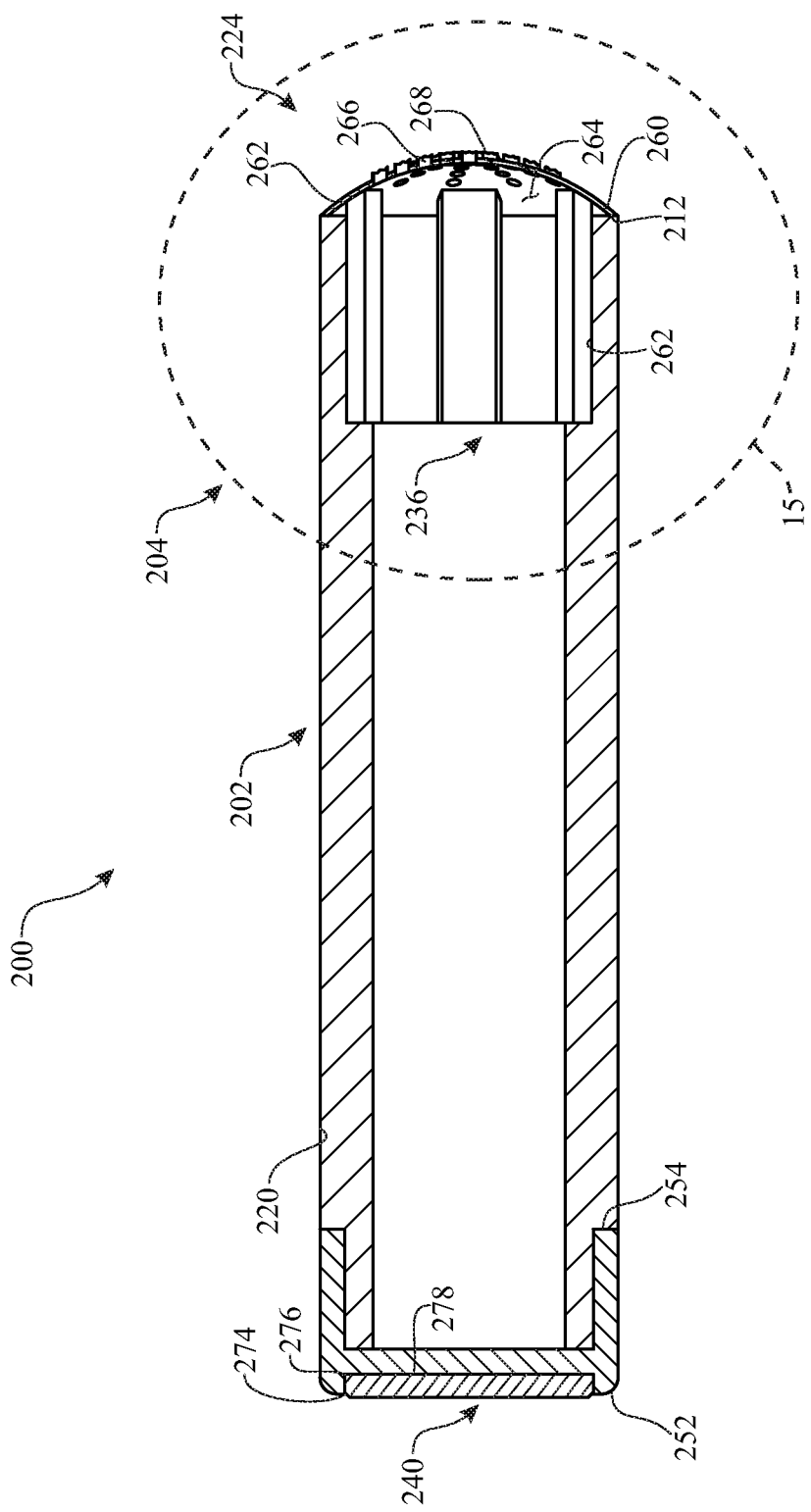
FIG. 14 presents a longitudinal sectional assembled view of the alternate embodiment of the callus scraping device taken along section line 14-14 in FIG. 13.
Figure 15:
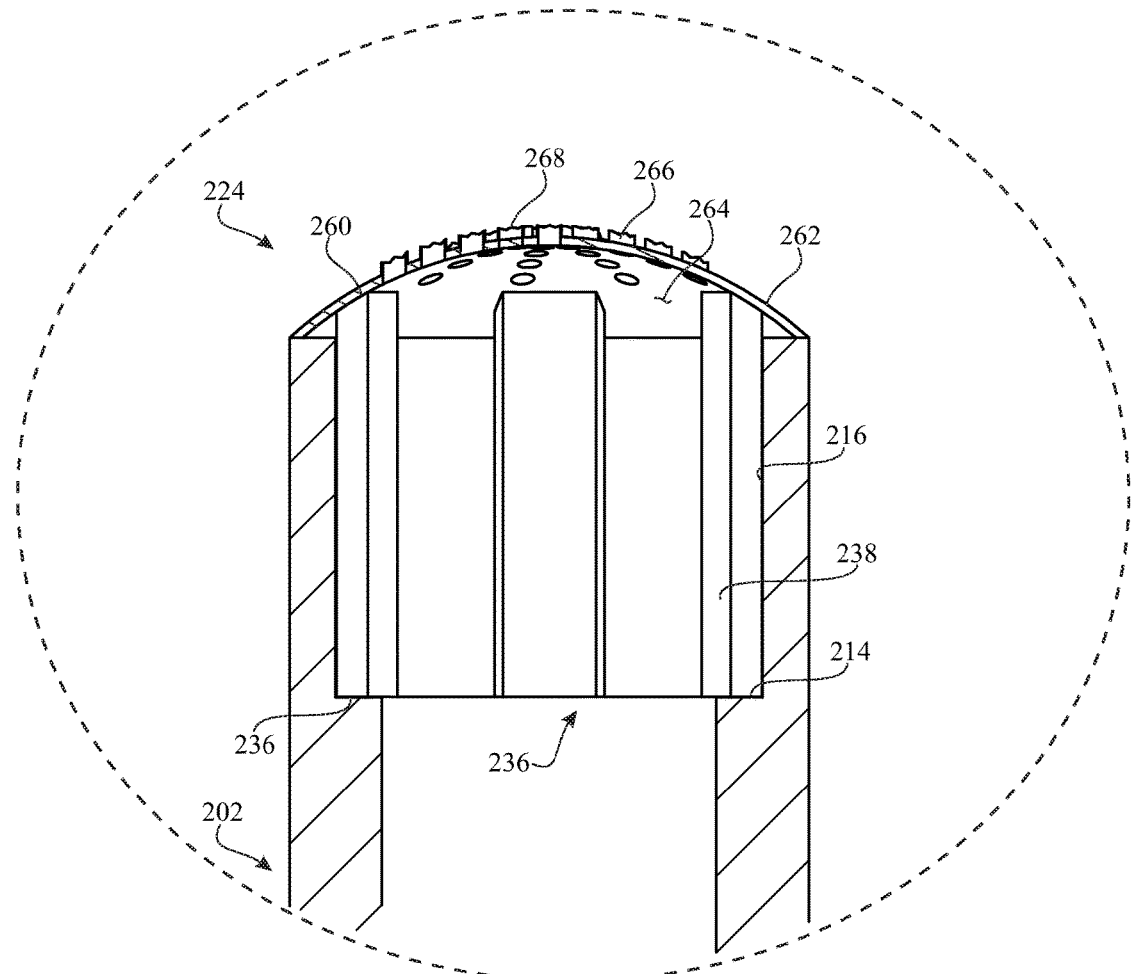
FIG. 15 presents an enlarged view of the upper end of the alternate embodiment of the callus scraping device taken along the dashed enclosed circle 15 of FIG. 14.

As is more clearly shown in FIGS. 12 through 15, the first end portion 208 of the main body has an annular end face 222 and an annular ledge 214 on the inside of the first end portion, being spaced longitudinally along the first end portion 208 from the annular end face 212, and extending inwardly from the first end portion such than an annular recess 216 is formed on the inside of and about the first end portion 208. The annular end face 212 extends longitudinally approximately from the annular end face 212 to the annular ledge 214 (as better shown on FIG. 15). Turning now to FIGS. 12 and 14, the second end portion 210 of the main body 202 has an annular end face 218 and an annular ledge 220 on the outside of the second end portion, being approximately spaced longitudinally along the second end portion 210 from the annular end face 218, and extending outwardly from the second end portion such that an exterior annular recess 222 is formed outside of and approximately about the second portion 210.

Generally, the head 224 of the callus scraping device 204 includes a wall that has an exterior upper wall surface 262 and an interior lower wall surface 264. Exposed at the exterior upper wall surface 262 is a plurality of spaced-apart punched-through projections 266 projecting upwardly from wall 260 and forming a plurality of upper jagged edges 268 at a distal end of the projections 266. The spaced-apart punched-through portions are arranged in a circular configuration and radiate from a peak point 272 to approximately the annular peripheral edge 234 of head 224. The callus scraping device 204 head 224 is generally formed of a convex or dome-like shape which allows for the jagged edges 268 of the punched-through portions 266 of wall 260 capable of making contact and removing pieces of callus when moved in any direction and in contact with a callus.

The head 224 of the callus scraping device 204 also annular peripheral edge 234 surrounding the exterior and interior surfaces 262, 264 and the plurality of spaced-apart punched-through projections 226 that extend through the wall 260. Furthermore, the device 204 also includes a connector 236 in the form of a plurality of legs 238 arranged spaced-apart from one another in a circular manner and fixedly attached to the interior lower surface 264 of head 224. The legs 238, generally, are made of a resilient springy material in order for the legs 238 to yield sufficiently inwardly to snugly press-fit within the first portion 208 of the hollow main body 202 as at least one of the annular peripheral edge 234 of head 224 make contact with the annular end face 212 of the main body 202 or the connector 236 at a rear end thereof make contact with the annular ledge 214 on the inside of the first end portion 208 of the main body (see FIG. 15).

Opposite the head scraping device 204, the callus sanding device 206, as shown on FIGS. 12 and 14, generally include a panel 240 having an exterior face 242, and a plurality of sanding particles 244 attached on the exterior face of the panel. The sanding particles 244 are exposed and thus capable of contacting, and removing pieces of, a callus. The panel 240 with the sanding particles 244 may be in the form of a piece of 80 GHT sandpaper, however, other types of course material may be employed. As shown on FIGS. 12 and 14, the panel 240 of the callus sanding device 206 includes an interior face 248 and an annular peripheral rim portion 250 surrounding the exterior and interior faces 242, 248 and the plurality of sanding particles 244 on the exterior face. The cap 246 has a recess 273 provided for receiving the panel 240 therein. The recess 273 approximately extends longitudinally from a first edge 274 to a second edge 276 on top surface 278. The callus sanding device 206 may also be joined with the end cap 246 received in the annular recess 222 so as to snugly fit about the outside of the second end portion 210 of the main body 202.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A callus removal apparatus, comprising:
    a hollow main body having an elongated form for ease of gripping said hollow main body with one hand, said hollow main body comprising:
        opposite first and second end portions where a longitudinal axis extends between said first and second end portions, and
        an opening disposed at said first end portion and extending transversely to the longitudinal axis, said opening being in fluid communication with a hollow interior of the main body;
    a callus scraping element disposed on said first end portion of said main body, said callus scraping device comprising:
        a head extending over said opening, said head having an exterior surface of convex shape and an interior surface, and
        an array of spaced-apart punched-through projections extending upwardly from said exterior surface of said head, each of said punched-through projections terminating at a jagged peripheral edge at a distal end thereof, said head being capable of frictionally contacting and removing pieces of a callus via frictional rubbing engagement of said head with an exterior surface of the callus; and
    a callus sanding device fitted on said second end portion of said main body, said callus sanding device comprising:
        a panel having an exterior face where said panel extends transversely with respect to the longitudinal axis, and
        a plurality of sanding particles attached on said exterior face of said panel and exposed at the exterior thereof, said sanding particles being capable of frictionally contacting and removing pieces of a callus via frictional rubbing engagement of said sanding particles with an exterior surface of the callus,
    wherein at least one of said callus scraping element and said callus sanding device are removably fitted to said main body providing access to said hollow interior such that during use, pieces of callus collected within the hollow interior may be discarded by removal of said at least one of said callus scraping device and said callus sanding device.

2. The callus removal apparatus as recited in claim 1 wherein
    said first end portion of said main body has an annular end face and an annular ledge on an inside of said first end portion being spaced longitudinally along said first end portion from said annular end face and extending inwardly from said first end portion such that an annular recess is formed on the inside of and about said first end portion and extends longitudinally from said annular end face to said annular ledge.

3. The callus removal apparatus as recited in claim 1 wherein the spaced-apart punched-through projections are provided in an annular configuration and radiate outwardly from a peak on said head to an annular peripheral edge of said head, said annular peripheral edge surrounding said exterior and interior surfaces and said plurality of spaced-apart punched-through projections which extend between said interior and exterior surfaces of said head providing a plurality of corresponding spaced-apart apertures.

4. The callus removal apparatus as recited in claim 3 wherein said callus scraping device also comprises of a connector fixedly attached to said interior surface of said head inside of said annular peripheral edge of said head, surrounding said plurality of spaced-apart punched-through projections, and extending away from said head so as to snugly fit within said first end portion of said main body as at least one of said annular peripheral edge portions of said head makes contact with said annular end face of said main body, or said connector at a rear end thereof makes contact with said annular ledge on the inside of said first end portion of said main body.

5. The callus removal apparatus as recited in claim 1 wherein
said callus sanding device is joined with an end cap at one end fitted on said second end portion of said main body and detachable from said main body to remove callus pieces from said main body, said end cap at an opposite end supporting said panel.

6. The callus removal apparatus as recited in claim 1 wherein
said second end portion of said main body has an annular end face and an annular ledge on an outside of said second end portion being spaced longitudinally along said second end portion from said annular end face and extending outwardly from said second end portion such that an annular recess is formed outside of and about said second end portion and extends longitudinally from said annular end face to said annular ledge.

7. The callus removal apparatus as recited in claim 6 wherein:
said panel of said callus sanding device has an interior face opposite the exterior face and an annular peripheral rim portion surrounding said exterior and interior faces and said plurality of sanding particles on said exterior face, wherein said annular peripheral rim portion of said panel is supported at a top surface of a second recess on said end cap; and
said callus sanding device is joined with an end cap received in said annular recess so as to snugly fit about the outside of said second end portion as said end cap makes contact with said annular ledge on the outside of said second end portion of said main body.

8. A callus removal apparatus, comprising:
a hollow main body having an elongated configuration for ease of gripping said hollow main body with one hand, said hollow main body comprising:
opposite first and second end portions where a longitudinal axis extends between said first and second end portions, and
an opening disposed at said first end portion and extending transversely to the longitudinal axis, said opening being in fluid communication with a hollow interior of the main body;
a callus scraping device fitted on said first end portion of said main body, said callus scraping device comprising:
a head extending over said opening, said head having a concave-shaped exterior surface, and
an array of spaced-apart punched-through projections extending upwardly from said exterior surface of said head, each of said punched-through projections terminating at a jagged peripheral edge at a distal end thereof, said head being capable of frictionally contacting and removing pieces of a callus via frictional rubbing engagement of said head with an exterior surface of the callus;
a callus sanding device fitted on said second end portion of said main body, said callus sanding device comprising:
a panel having a planar exterior face where said panel extends transversely with respect to the longitudinal axis, and
a plurality of sanding particles attached on said planar exterior face of said panel and exposed at said exterior thereof and thus capable of contacting and removing pieces of a callus by moving said panel across and in contact with the callus,
wherein at least one of said callus scraping element and said callus sanding device are removably fitted to said main body providing access to said hollow interior such that during use, pieces of callus collected within the hollow interior may be discarded by removal of said at least one of said callus scraping device and said callus sanding device.

9. The callus removal apparatus as recited in claim 8 wherein the spaced-apart punched-through projections are provided in an annular configuration and radiate outwardly from a peak on said head to an annular peripheral edge of said head, said annular peripheral edge surrounding said exterior and interior surfaces and said plurality of spaced-apart punched-through projections which extend between said interior and exterior surfaces of said head providing a plurality of corresponding spaced-apart apertures.

10. The callus removal apparatus as recited in claim 8 including an end cap fitted on and enclosing said second end portion of said hollow main body and being detachable from said hollow main body to remove callus pieces from said hollow main body; where said callus sanding device is fitted on and joined with said end cap.

11. The callus removal apparatus as recited in claim 8 wherein said first end portion of said main body has an annular end face and an annular ledge on an inside of said first end portion being spaced longitudinally along said first end portion from said annular end face and extending inwardly from said first end portion such that an annular recess is formed on the inside of and about said first end portion and extends longitudinally from said annular end face to said annular ledge.

12. The callus removal apparatus as recited in claim 9 wherein said callus scraping device also comprises of a connector fixedly attached to said interior surface of said head inside of said annular peripheral edge of said head, surrounding said plurality of spaced-apart punched-through projections, and extending away from said head so as to snugly fit within said first end portion of said main body as at least one of said annular peripheral edge portions of said head makes contact with said annular end face of said main body, or said connector at a rear end thereof makes contact with said annular ledge on the inside of said first end portion of said main body.

13. The callus removal apparatus as recited in claim 8 wherein said second end portion of said main body has an annular end face and an annular ledge on an outside of said second end portion being spaced longitudinally along said second end portion from said annular end face and extending outwardly from said second end portion such that an annular recess is formed outside of and about said second end portion and extends longitudinally from said annular end face to said annular ledge.

14. The callus removal apparatus as recited in claim 8 wherein said panel of said callus sanding device also has an interior face and an annular peripheral rim portion surrounding said exterior and interior faces and said plurality of sanding particles on said exterior face, wherein said annular peripheral rim portion of said panel is supported at a top surface of a second recess on said end cap; and said callus sanding device is also joined with an end cap received in said annular recess so as to snugly fit about the outside of said second end portion as said end cap makes contact with said annular ledge on the outside of said second end portion of said main body.

* * * * *